US008053248B2

(12) United States Patent
Bakaltcheva et al.

(10) Patent No.: US 8,053,248 B2
(45) Date of Patent: Nov. 8, 2011

(54) SUPPORT SYSTEM FOR FLEXIBLE LYOPHILIZATION CONTAINERS

(75) Inventors: Irina Bakaltcheva, Springfield, VA (US); Donna Wilder, Washington, DC (US); Peter Hmel, Gaithersburg, MD (US); Anne-Marie O'Sullivan, Silver Spring, MD (US); Lloyd Ketchum, Washington, DC (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 857 days.

(21) Appl. No.: 11/573,669

(22) PCT Filed: Aug. 12, 2005

(86) PCT No.: PCT/US2005/028619
§ 371 (c)(1),
(2), (4) Date: Jan. 2, 2008

(87) PCT Pub. No.: WO2006/028648
PCT Pub. Date: Mar. 16, 2006

(65) Prior Publication Data
US 2008/0119818 A1    May 22, 2008

Related U.S. Application Data

(60) Provisional application No. 60/601,184, filed on Aug. 13, 2004.

(51) Int. Cl.
*F26B 5/06* (2006.01)

(52) U.S. Cl. ............... 436/176; 34/92; 34/284; 604/403; 604/408; 426/384

(58) Field of Classification Search .................. 34/284, 34/92; 604/403, 408; 436/176; 426/384
See application file for complete search history.

(56) References Cited

U.S. PATENT DOCUMENTS

| 4,173,676 | A | 11/1979 | Asakura et al. |
| 4,973,327 | A | 11/1990 | Goodrich, Jr. et al. |
| 5,560,480 | A | 10/1996 | Singleton |
| 6,517,526 | B1 * | 2/2003 | Tamari ..................... 604/403 |

* cited by examiner

*Primary Examiner* — In Suk Bullock
*Assistant Examiner* — Paul Hyun
(74) *Attorney, Agent, or Firm* — Novak Druce & Quigg, LLP

(57) ABSTRACT

A suitable container for plasma lyophilization has been designed for lyophilization (lyo-bag), storage, reconstitution and administering of blood products. A rigid support frame for use with a lyo-bag with sidewalls was designed as an external removable supportive system, which provides the necessary stability for the flexible container during lyophilization. A removable bottom wall support sheet was designed for use with any flexible container for lyophilization.

6 Claims, 7 Drawing Sheets

SUPPORT SYSTEM FOR FLEXIBLE LYOPHILIZATION CONTAINERS

REFERENCE TO RELATED APPLICATIONS

This invention claims priority to U.S. Provisional Application No. 60/601,184 entitled "Support System for Flexible Lyophilization Containers" filed Aug. 13, 2004, the entirety of which is hereby specifically incorporated by reference.

RIGHTS IN THE INVENTION

This invention was made, in part, with support from the U.S. Government under the Combat Casualty Care Program, U.S. Army Fund No. 600-235-00000-00 03348, and, accordingly, the U.S. Government may have certain rights in this invention.

BACKGROUND OF THE INVENTION

1. Field of the Invention

This invention is directed to support systems and containers for lyophilization and methods for lyophilization with flexible containers.

2. Description of the Background

Fresh Frozen Plasma (FFP) is essential for the clinical management of coagulopathies associated with combat trauma. However, the frozen formulation has three major limitations, which reduce its far forward availability in the field. First, FFP must be stored at −30° C. in freezers. Second, the number of FFP units transshipped is restricted by the dry ice ($CO_2$) limitation of air transport. And finally, this creates a need for bulky and expensive processing equipment along with sufficient time to properly thawed the units before transfusion. Processing times are typically from 30 to 40 minutes, but can on occasion be longer.

Several containers have been recently introduced, which permit lyophilization of products to take place in an enclosed system omitting the risk of contamination during the lyophilization process and in line with FDA requirements for blood processing (FIGS. 1-5). Such containers commonly feature hydrophobic protective membranes. The membranes contain pores, which are permeable to water vapor but, on the other hand, are sufficiently small (<0.2 µm) so as to prevent microorganisms from passing through. Membrane permeability to water vapor permits product drying inside these closed containers. Membrane impermeability to microorganisms adds a protective feature to these containers to classify them as enclosed systems. Membrane impermeability to fluids makes these containers suitable for direct rehydration.

These containers come in two basic formats: flexible (FIGS. 1, 2) and rigid (FIGS. 3-5). Rigid containers feature solid side walls and possess the required stability to withstand the stress of freeze-drying, particularly the strain imposed by the vacuum during the process. These containers, however, cannot be collapsed after completion of the lyophilization process. Flexible containers, on the other hand, typically feature a pliable bottom wall, a pliable top wall incorporating a breathable membrane, and side walls sufficiently rigid to support the top wall, but also sufficiently flexible to collapse and minimize storage space once lyophilization is complete (FIG. 1). The container structure is intended to be sufficiently rigid to sustain the stress imposed by the lyophilization process, but is also flexible enough to be collapsed after lyophilization, thereby reducing storage space and offering a logistical advantage.

U.S. Pat. No. 6,517,526 (which is entirely and specifically incorporated by reference) relates to a lyophilization system and discloses a thermally conductive tray which serves as its support system. The tray defines at least one cavity having a cavity floor and a depth that accommodates the lyo-container. The support system further includes a rigid mating flange, which overlays the supporting tray, cooperating with the tray, to secure landing of the lyo-container during lyophilization. Although this support system allows for handling of the container in a more convenient way, it is neither intended to prevent folding of the flexible bottom under vacuum, nor to assure a flat fixture of the top pliable membrane prior to or during lyophilization.

A flexible container developed by Foster-Miller Corp. features a supportive system. That system contains a plastic rigid internal ring on top of which is secured a pliable membrane. The rigid ring assures a flat fixed shape of the pliable membrane prior to and during lyophilization. However, removing the ring from the internal container structure is required to collapse the container after lyophilization and to take advantage of its flexible nature, although this latter process is not clearly defined.

To remedy the storage, shipment and processing problems and to bring plasma far forward in the field, a freeze-dried whole plasma product stable at ambient temperature was developed. The process of plasma lyophilization is carried out in glass bottles in an open space environment. However, at least two problems are associated with these containers that obstruct their successful realization in the hospital and/or the field. First, the containers are glass and glass, although rigid, is not a blood bank/hospital compatible container and cannot be used in transfusion practice. Second, product processing and lyophilization typically occur in an open space environment thus exposing the product to contaminants. However, FDA regulations do not permit blood processing in an open environment.

A container for plasma lyophilization called the lyo-bag was developed by Circulatory Technology Inc. (FIGS. 1-2). However, two problems associated with the container structure (FIG. 2) inhibited its successful utilization. First, the side walls of the container do not provide sufficient support to the top membranous wall. As a result, the flexible membrane collapses over the fluid in the container before and/or during the process of lyophilization as vacuum stresses the container. Contamination of the breathable membrane with the product blocks its porous structure and inhibits water vapor removal through it, resulting in a partially dried product (FIG. 3).

Also, the flexible bottom wall folds upwards during the process of lyophilization, particularly, as vacuum is applied to the system. The folded flexible bottom wall no longer provides an intimate thermal contact with the cooling/heating shelf of the freeze-dryer. As a consequence, pockets with incompletely dried product are formed (FIG. 4), which renders the resulting material useless. Thus, a need exists for suitable containers for plasma lyophilization.

SUMMARY OF THE INVENTION

The present invention overcomes the problems and disadvantages associated with current strategies and designs and provides new support systems and containers for lyophilization and methods for lyophilization with flexible containers.

One embodiment of the invention is directed to a support structure for lyopliilizing a fluid comprising a rigid frame that supports side walls of a flexible lyophilization container; and a support sheet for reducing flexibility of a bottom wall of the flexible lyophilization container to allow for successful lyophilization of said fluid. The support sheet, which is magnetic, is removable affixed to the container by a double-sided tape, which is a thermo-stable tape.

Another embodiment of the invention is directed to a support structure for lyophilizing a fluid comprising a support sheet for reducing flexibility of a bottom wall of a flexible lyophilization container to allow for successful lyophilization of said fluid. The support sheet is magnetic, removable and affixed to the container with double-sided tape that is thermo-stable.

Another embodiment of the invention is directed to a method of providing adequate support to a flexible lyophilization container during the process of lyophilizing a biological solution in the flexible lyophilization container comprising securing a side or top wall of the lyophilization container to a support frame; and affixing a bottom flexible wall of the lyophilization container to a magnetic support sheet with thermally conductive double-sided tape. The support frame is removable and is secured to said lyophilization container by pins.

Another embodiment of the invention is directed to a support system for lyophilizing a biological solution in a lyophilization container comprising a flexible lyophilization container; a hydrophobic protective GORE-TEX™ porous membrane attached at a top surface of the flexible lyophilization container; and a support sheet affixed to a bottom wall of the lyophilization container.

Another embodiment of the invention is directed to a method of providing adequate support to a flexible lyophilization container during the process of lyophilizing a biological solution in the flexible lyophilization container comprising providing a flexible lyophilization container having a first top flexible membrane and an inward directed plastic strip to which the top flexible membrane is attached; removing the first top flexible membrane along with the inward directed plastic strip; attaching an outward directed plastic strip to a top edge of the flexible lyophilization container to serve as a platform for a replacement GORE-TEX™ membrane; affixing the replacement GORE-TEX™ membrane to the top edge of the flexible lyophilization container; affixing a bottom flexible wall of the lyophilization container to a magnetic support sheet with thermally conductive double-sided tape; and placing the support sheet on a steel tray.

Other embodiments and advantages of the invention are set forth in part in the description, which follows, and in part, may be obvious from this description, or may be learned from the practice of the invention.

DESCRIPTION OF THE INVENTION

Figure 1:
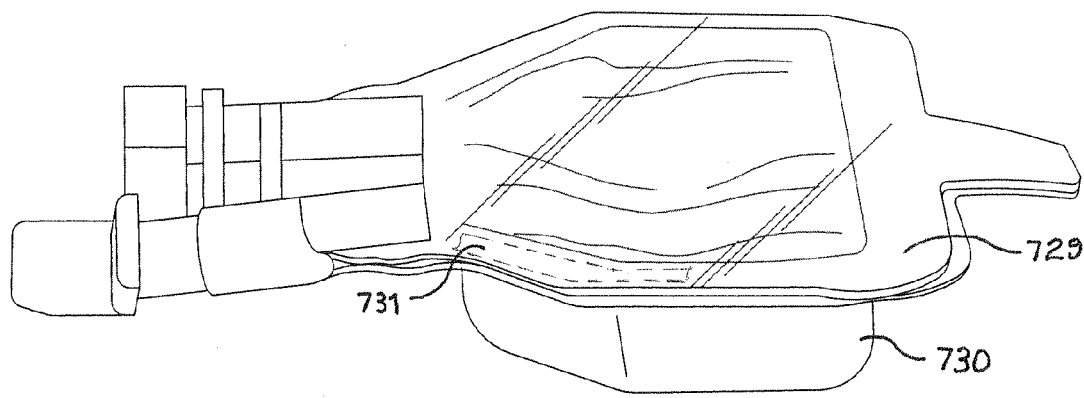
FIG. 1 (prior art). Flexible Lyo-Bag (CircTech, Inc.). The bag was constructed of a biocompatible film and incorporated a large 0.2-µm-pore-size hydrophobic membrane. The membrane allows water vapor transport during the lyophilization process, while acting as a sterile barrier.

Flexible containers for lyophilization, storage, reconstitution and administering of biological solutions and, in particular, blood products have been recently introduced (Tamari, Y. Container for lyophilizing biological products. U.S. Pat. No. 6,517,526; Gilman, V. "Development of a Flexible Container (Bag) for Lyophilization of Blood Products". Lyophilization and Freeze-Drying Conference, Sep. 13-19, 2003 Chicago, Ill.).

Such containers generally feature a pliable bottom wall, a pliable top wall incorporating a breathable membrane, and side walls sufficiently rigid to support the top wall. These containers are also sufficiently flexible to collapse and minimize storage space once lyophilization is complete. However, problems associated with this flexible container structure were found.

A surprising and elegant support system was designed to remedy these and other problems associated with storage, transportation and use of lyophilization contains, that allows for successful lyophilization of whole units of blood products and other biological materials. A successful lyophilization includes prevention of folding of the bottom flexible wall of a lyophilization container. The lyophilization support system of the invention comprises a solid removable frame that supports the top wall of the container. In particular, the top membranous wall is secured on top of the solid walls of the removable frame. This structure stabilizes the pliable membrane and keeps that membrane from contacting product before and during the lyophilization process.

During lyophilization, a sheet, which may be flexible or rigid, is fixed to the bottom wall. Preferably the sheet is a flexible magnetic sheet that can be easily attached to the bag. Attachment may be by an adhesive, double-sided tape, or with any conventional attachment, and is preferably a durable adhesive or double-sided, thermo-stable tape. The container is then placed on a tray to conduct lyophilization. When the tray is steel or otherwise magnetic, a magnetic sheet is preferred and the magnetic force between the magnetic sheet and the steel tray keeps the pliable bottom wall from folding under vacuum thus securing an intimate thermal contact with the shelf during lyophilization. Thus, the flexible sheet is sufficiently rigid during lyophilization to prevent folding or otherwise wrinkling of the container.

After completion of lyophilization, the flexible container is detached from the supportive frame and also the sheet. The container with the completely dried product is now ready to be collapsed and sealed under vacuum. Collapsing the container minimizes storage space and serves logistical purposes.

The invention delivers an external, removable, easy-to-use support system for flexible lyophilization containers ("lyo-containers"). Any flexible lyo-container can be used in conjunction with the invention described herein to successfully lyophilize whole units of human plasma, biological materials (e.g. platelets, immunoglobulin, immunological factors) or most any fluid. Rigid containers are also used for lyophilization, but do not collapse when subjected to a vacuum process. In contrast, a flexible container collapses when subjected to a vacuum process providing both cost and space efficiency during transportation and storage of the containers.

Flexible lyo-containers are bags of a continuous membrane and typically hold from 25 mL to 1 L, or more, of fluid. Bags may be manufactured to hold nearly any amount of fluid, such as less than 25 mL and more than 1 L, but preferably hold 50 mL, 75 mL, 100 mL, 150 mL, 200 mL, 2500 mL, 300 mL, 350 mL, 400 mL, 500 mL, 600 mL, 700 mL, 800 mL, 900 mL, or 1 L. Bags can be of any shape including, but not limited to, spherical, oval, or circular, but are most typically square or rectangular. The sides of the bag represent the outline of the shape, with the top and bottom sides interchangeable, referencing only which side happens to be facing up when the container is placed on a surface.

The support system of the invention features an external solid frame which secures a flat fixed shape of the pliable membrane and is easy to remove after completion of lyophilization. This is the first support system featuring a removable bottom. When the removable bottom is magnetic, the magnetic force between the magnetic bottom and the steel tray keeps the pliable container bottom from folding under vacuum, thus securing intimate thermal contact with the shelf during lyophilization.

Another embodiment of the invention is a rectangular container featuring a flexible plastic dish comprised of a flexible bottom wall, and four flexible side walls, which end into an outward directed platform. The outward directed platform serves as a support structure on top of which a hydrophobic protective membrane is sealed. This particular way of attachment provides sufficient support for the membrane and prevents it from sagging and contacting the product enclosed into the container. Membrane pore sizes are typically less than 0.65 μm, less than 0.45 μm, and preferably 0.2 μm.

The flexible membrane of a lyophilization container (commercially available from Circulatory Technology Inc.) was cut out along with the inward directed plastic strip to which it was attached. Then, an outward directed plastic strip was attached to the top edge of the plastic dish to serve as a platform for the new membrane. A GORE-TEX™ membrane (expanded polytetrafluoroethylene generally sold in film form, W.L. Gore & Associates, Inc.) was sealed on top of the outward directed platform. Any other crtical, non-reactive porous membrane material that can withstand environmental factors including typical lyophilization and storage temperatures and pressures may be used as the replacement membrane (e.g. Tyvek™ a nonwoven spunbonded olefin generally sold in sheet form, DuPont™). Existing lyo-container designs do not incorporate a platform as an extension of the side walls to serve as a natural, part of the container, support structure to the membrane. Existing lyo-container designs outline an inward-directed mode of membrane attachment, that additionally contributes to membrane instability, sagging, and product-contacting The flexible lyophilization container was then affixed to a removable support bottom. The support bottom is preferably magnetic to provide a magnetic force between the magnetic bottom and the steel tray. This keeps the pliable container bottom from folding under vacuum, thus securing intimate thermal contact with the shelf during successful lyophilization.

One embodiment of the invention is directed to a container comprising a solid removable frame to support the top wall of the container. In particular, the top membranous wall is secured on top of the solid walls of the removable frame. This may be achieved by appropriate securing devices, including but not limited to, pins, glue, tape and magnets. This support structure stabilizes the pliable membrane and keeps it from contacting the product before and during the process of lyophilization.

A flexible support sheet is attached to the bottom wall via, preferably, a double-sided tape. The container is then placed on a steel tray to conduct a successful lyophilization. The flexible support sheet is preferably a magnetic material. The magnetic force between the magnetic sheet and the steel tray keeps the pliable bottom wall from folding under vacuum, thus securing an intimate thermal contact with the shelf during lyophilization.

The support sheet provides adequate support to the pliable bottom during the process of lyophilization. Therefore, the support sheet for flexible lyo-containers can be made of any suitable material, providing such support sheets are sufficiently rigid, to assure solid contact between the tray and the flexible bottom during lyophilization. It is preferred that the material have good heat conducting properties to facilitate heat transfer fiom the shelf of the lyophilizer to the bottom of the lyo-container.

The support sheets can be attached to the pliable bottom of the lyophilization container via a variety of double-sided adhesive tapes. However, thermally conductive adhesive tape is preferred. Thermally conductive tapes are manufactured by coating a woven glass fiber web, dielectric film or aluminum foil substrate on which both sides are coated with either a silicone or acrylic based (or sometimes both) adhesive, impregnated with thermally conductive particles (e.g. ceramic, Boron Nitride, graphite, alumina, and other similar and conventionally available materials). Silicone based adhesives are preferred when attaching to low energy surfaces (like plastics) while acrylic based adhesives are best for metal-to-metal joints. Such tapes have a dual role participating as an interface material and as an attachment method.

Although freeze-drying in a magnetic field is described, uses beyond the supportive system described herein are clear to those skilled in the art. The strong magnetic field orients and structures the water molecules (the solvent being removed), which results in a uniformly frozen solution and a uniform freeze-dried cake product. The latter is especially important when freeze-drying large volumes of material such as whole units of blood products.

The following examples demonstrate various, but not all embodiments of the invention, and should not be viewed as limiting the scope of the invention.

EXAMPLES

The Supportive System

First Embodiment

Figure 5:
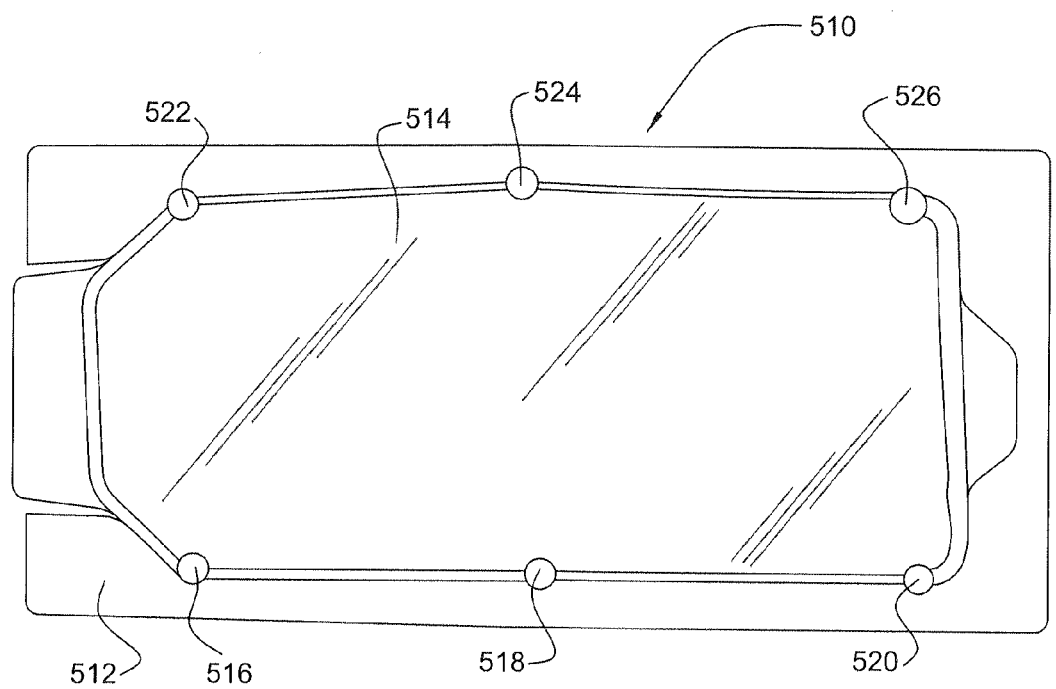
FIG. 5. Implementing the supportive system showing the top flexible membranous wall secured on top of the solid walls of a removable frame, keeping the membrane from contacting the product before and during lyophilization.

1. A solid removable frame (512) is used to support the top wall (514) of the container (510). In particular, the top membranous wall is secured on top of the solid walls of the removable frame using pins (516, 518, 520, 522, 524, 526). However, any other such attaching means for securing the top membranous wall to the top of the solid walls of the removable frame is acceptable, including but not limited to, adhesive tape, glue, screws, or magnets. This structure stabilizes the pliable membrane and keeps it from contacting the product before and during the process of lyophilization (FIG. 5).

Figure 6:
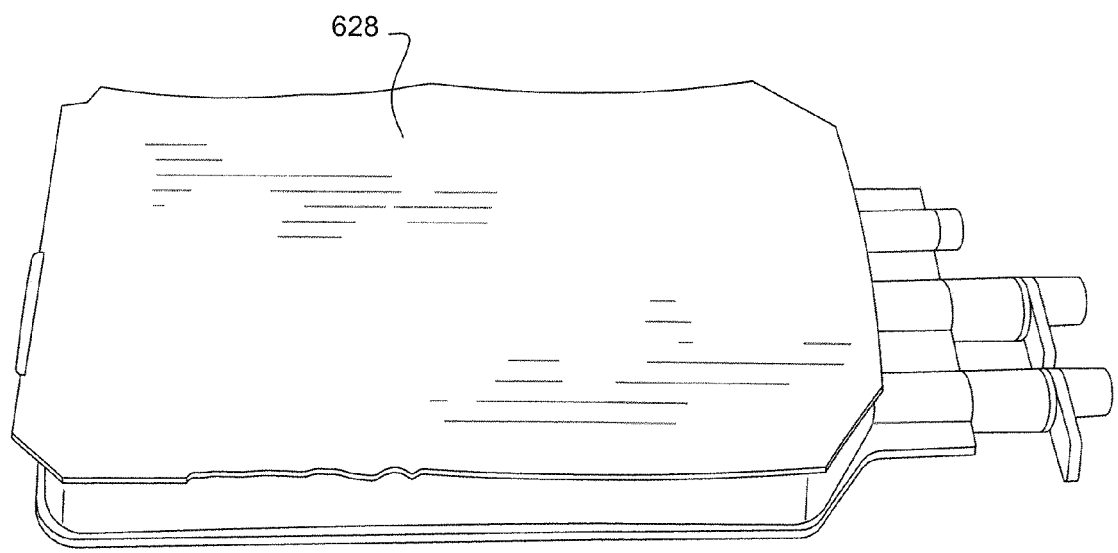
FIG. 6. Implementing the supportive system showing a flexible magnetic sheet attached to the bottom wall (bottom view). The container is then placed on a steel tray to conduct lyophilization. The magnetic force keeps the pliable bottom wall from folding under vacuum.

2. A flexible magnetic sheet (628) is attached to the bottom wall via a double-sided thermo-stable tape. The container is then placed on a steel tray to conduct lyophilization. The magnetic force between the magnetic sheet and the steel tray keeps the pliable bottom wall from folding under vacuum thus securing an intimate thermal contact with the shelf during lyophilization (FIG. 6). The bottom wall of the container may be affixed to the magnetic sheet by means other than a double-sided thermo-stable tape. Methods include, but are not limited to, magnets and glue. After completion of lyophilization the flexible container is detached from the supportive frame and the magnetic sheet. The container with the completely dried product is now ready to be collapsed and sealed under vacuum.

Second Embodiment

Figure 7:
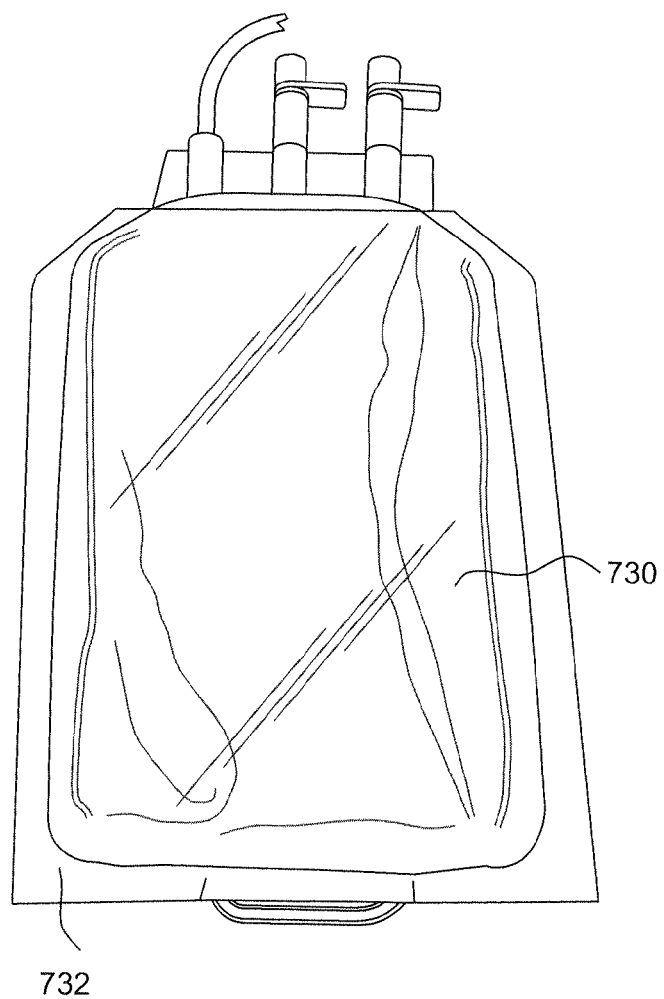
FIG. 7. Bottom view of flexible lyo-bag implementing the Gore-tex™ supportive system.
Figure 8:
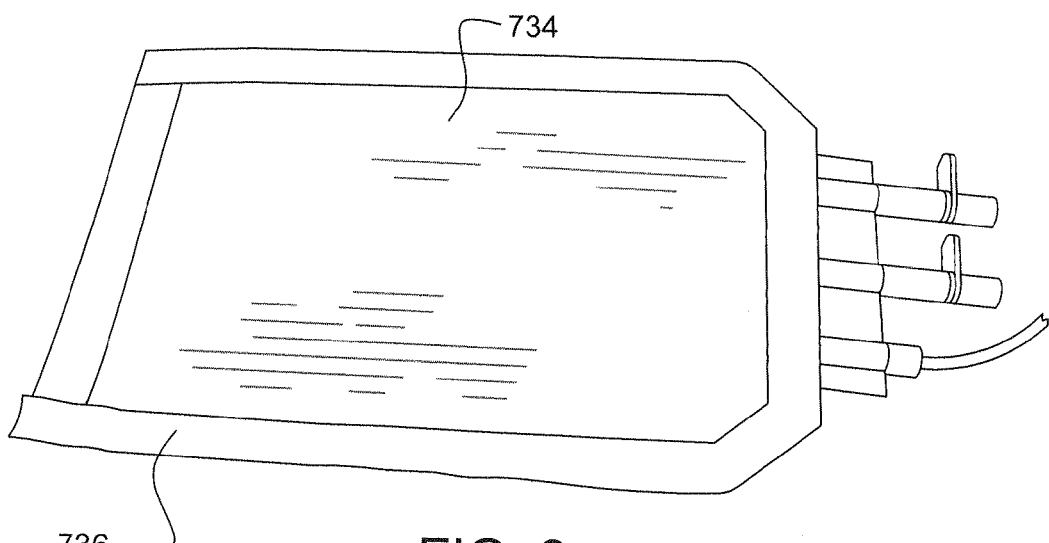
FIG. 8. Top view of flexible lyo-bag implementing the Gore-tex™ supportive system. The container is then placed on a steel tray to conduct lyophilization. The magnetic force keeps the pliable bottom wall from folding under vacuum.

1. A flexible lyophilization container (730) as in FIG. 1, was purchased from Circulatory Technology Inc. (FIG. 7). However, a blood bag manufactured by any company will suffice and can typically be made according to desired specification. The flexible membrane (729) from this container was cut out along with the inward directed plastic strip (731) to which it was attached. Then an outward directed plastic strip was attached to the top edge of the plastic dish to serve as a platform for the new membrane. A GORE-TEX™ membrane was then sealed on top of the outward directed platform (FIG. 8). This newly designed lyophilization container was then filled with 200 ml of plasma.

2. A flexible magnetic sheet was attached to the bottom wall via a double-sided thermo-stable tape. The container was then placed on a steel tray to conduct lyophilization. The magnetic force between the magnetic sheet and the steel tray keeps the pliable bottom wall from folding under vacuum thus securing an intimate thermal contact with the shelf during lyophilization (FIG. 6). The bottom wall of the container was affixed to the magnetic sheet by means other than a double-sided thermo-stable tape. Methods that can be used include, but are not limited to, magnets and glue. After completion of lyophilization the flexible container was detached from the supportive frame and the magnetic sheet. The container with the completely dried product was ready to be collapsed and sealed under vacuum. Flexible lyo-bags were used with or without the supportive system to lyophilize whole human plasma. Plasma coagulation properties in vitro are evaluated prior to and after lyophilization. Prothrombin time (PT), activated partial thromboplastin time (APTT), thrombin time (TT), fibrinogen, percentage activity of factors V and VIII levels were determined.

Material and Method

Figure 2:
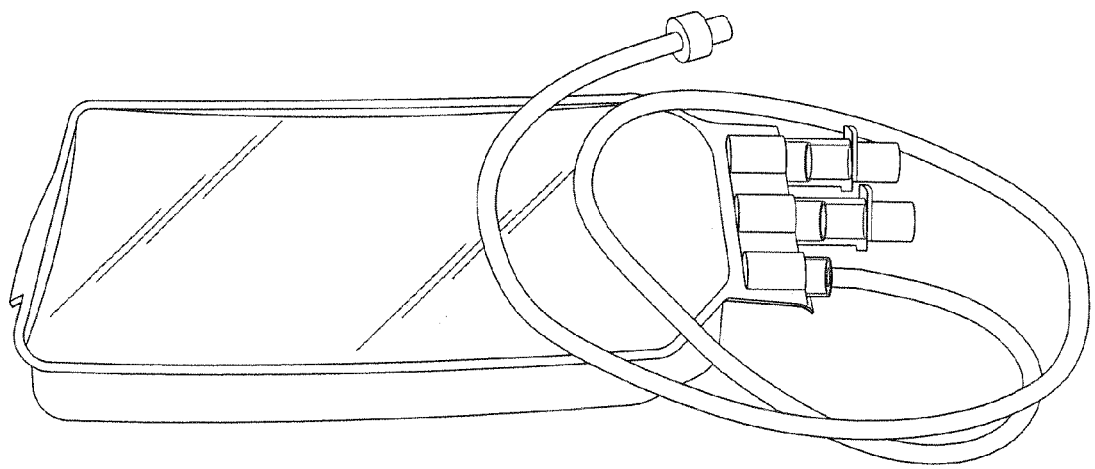
FIG. 2 (prior art). Flexible Lyo-Bag (CircTech, Inc.) after modifications per our request to serve the purpose of plasma lyophilization. (1) Increase in container size to hold up to 200 mL, and (2) incorporation of blood bank compatible tubing lines/ports.

Flexible lyo-containers were purchased from Circulatory Technology Inc., and used for plasma lyophilization, storage and reconstitution (FIG. 2). The Lyo-bags utilized were a: unmodified or b: in conjunction with one of the above described supportive systems. The magnetic sheets were purchased from Total Craft stores. A double-sided thermo-stable tape was purchased from Hugh Courtright and Co. The solid supportive frame was constructed using Foamboard. All reagents required to perform PT, APPT, TT, fibrinogen, Factor V and VIII percentage activity tests were obtained from Diagnostiga Stago.

Plasma Processing

Octaplas, a standardized, solvent-detergent (SD) virus inactivated plasma product was purchased from OctaPharma. Two hundred milliliters (200 ml) of Octaplas SD plasma were transferred from a standard blood bank bag into the lyo-bag using a sterile-docking device. The lyo-bag was used both with and without the supportive system to lyophilize Ocatplas SD plasma.

Lyophilization

Lyophilization was performed on the shelf of a TelStar freeze-dryer (LyoBeta 25) Primary drying was carried out at −26° C. Secondary drying was completed at 20° C. and the total lyo-cycle was conducted within 24 h.

Packaging

Two packaging modes were explored: 1) The lyo-bag containing the dry product was collapsed under vacuum and sealed in a moisture-resistant over-pouch using a retractable Sealer from Impak Corp. 2). The lyo-bag with the dry product was sterilely attached to a rehydration bag filled with the necessary amount of reagent grade water. The two bags where then sealed under nitrogen in a moisture-resistant overpouch. To ease shipment, the rehydration bag may be packaged empty and filled with water in the field.

Reconstitution

Lyophilized plasma was reconstituted directly in the lyo-container using a sterilely attached rehydration bag filled with the necessary amount of reagent grade water. Reconstitution may be accomplished also using a syringe instead of a bag.

Plasma Testing

A STA-R (Diagnostica Stago), automated coagulation instrument, was used to perform the following coagulation tests iil vitro: PT, APTT, TT, fibrinogen and Factor V and VIII percent activity. Standard procedures developed by Diagnostica Stago were followed (see Table 1).

Two hundred milliliters of Octa Plas SD plasma were lyophilized using a flexible lyo-bag in conjunction with the supportive system. Lyophilization was performed on the shelf of a TelStar freeze-Dryer (LyoBeta 25). The total lyo-cycle was conducted within 24 h. Lyophilized plasma was reconstituted directly in the lyo-bag using a sterilely attached rehydration bag filled with the necessary amount of water. A STA-R (Diagnostica Stago), automated coagulation instrument was used to perform the coagulation tests in vitro. Lyophilization resulted in minimal loss of coagulation activity.

1. Suitable lyo-containers for lyophilization of blood products, conforming to FDA regulations for blood processing in an enclosed system are identified (FIGS. 1-5).

2. Modifications to existing containers have been made to suit the specific application of plasma lyophilization, storage, reconstitution and administering (FIG. 2).

3. An external supportive system was designed and implemented, which provides the necessary stability for flexible lyo-containers during lyophilization (FIGS. 5, 6, 9, 10).

4. Using the flexible lyo-container in conjunction with the supportive system a 24 h long lyophilization cycle for whole human plasma was developed.

5. Plasma coagulation properties: Prothrombin time (PT), activated partial thromboplastin time (APTT), thrombin time (TT), fibrinogen, percentage activity of factors V and VIII were well preserved in the lyophilized plasma (Table 1).

Figure 11:
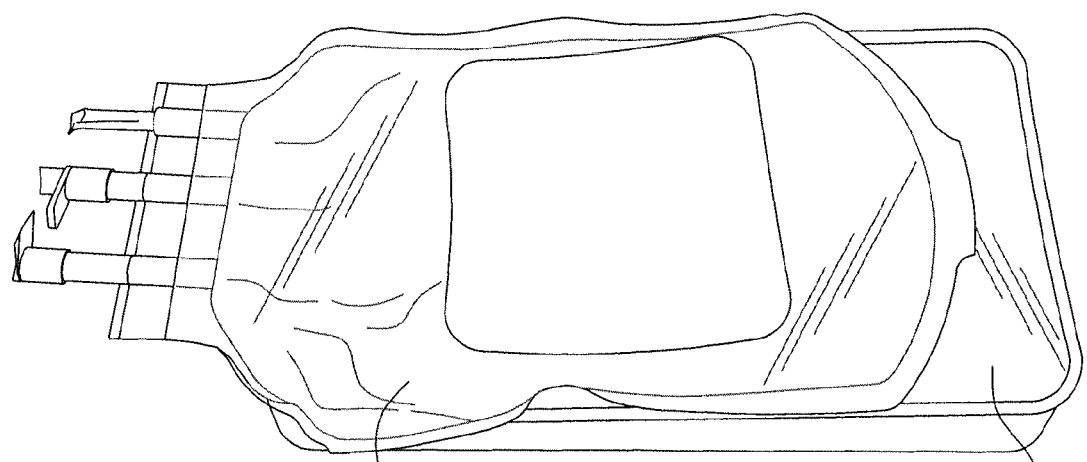
FIG. 11. Lyo-bag with the freeze-dried plasma sterilely attached to a rehydration bag with the necessary amount of reagent grade water.
Figure 13:
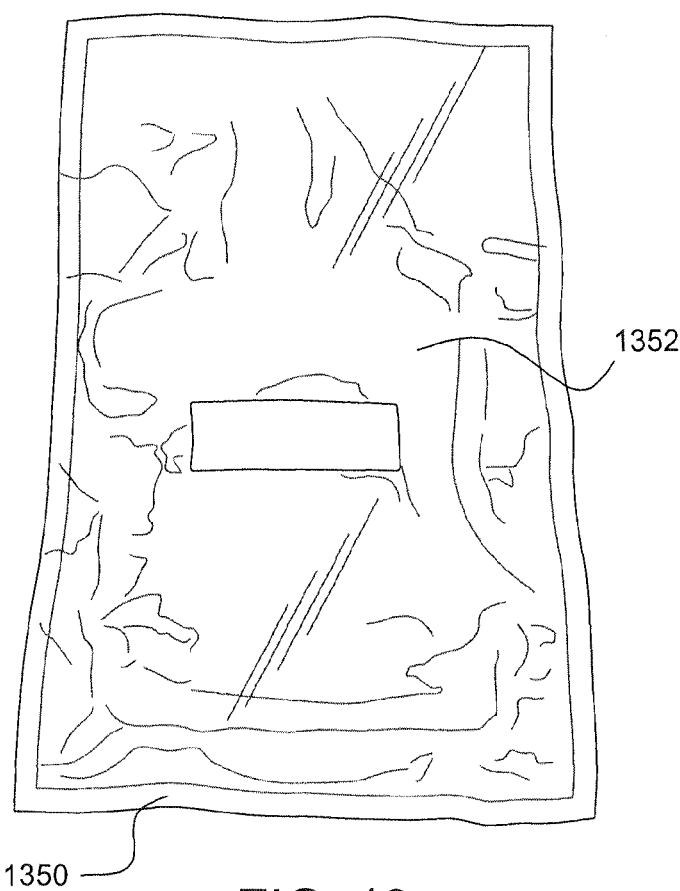
FIG. 13. A moisture-resistant overpouch is used to package the lyo-bag with the dry plasma and the rehydration bag. Two packaging modes can be utilized: 1) package the rehydration bag empty to ease the shipment and have it filled with water as it arrives in the field or 2) package the bag already filled with the necessary amount of reagent grade water.
Figure 12:
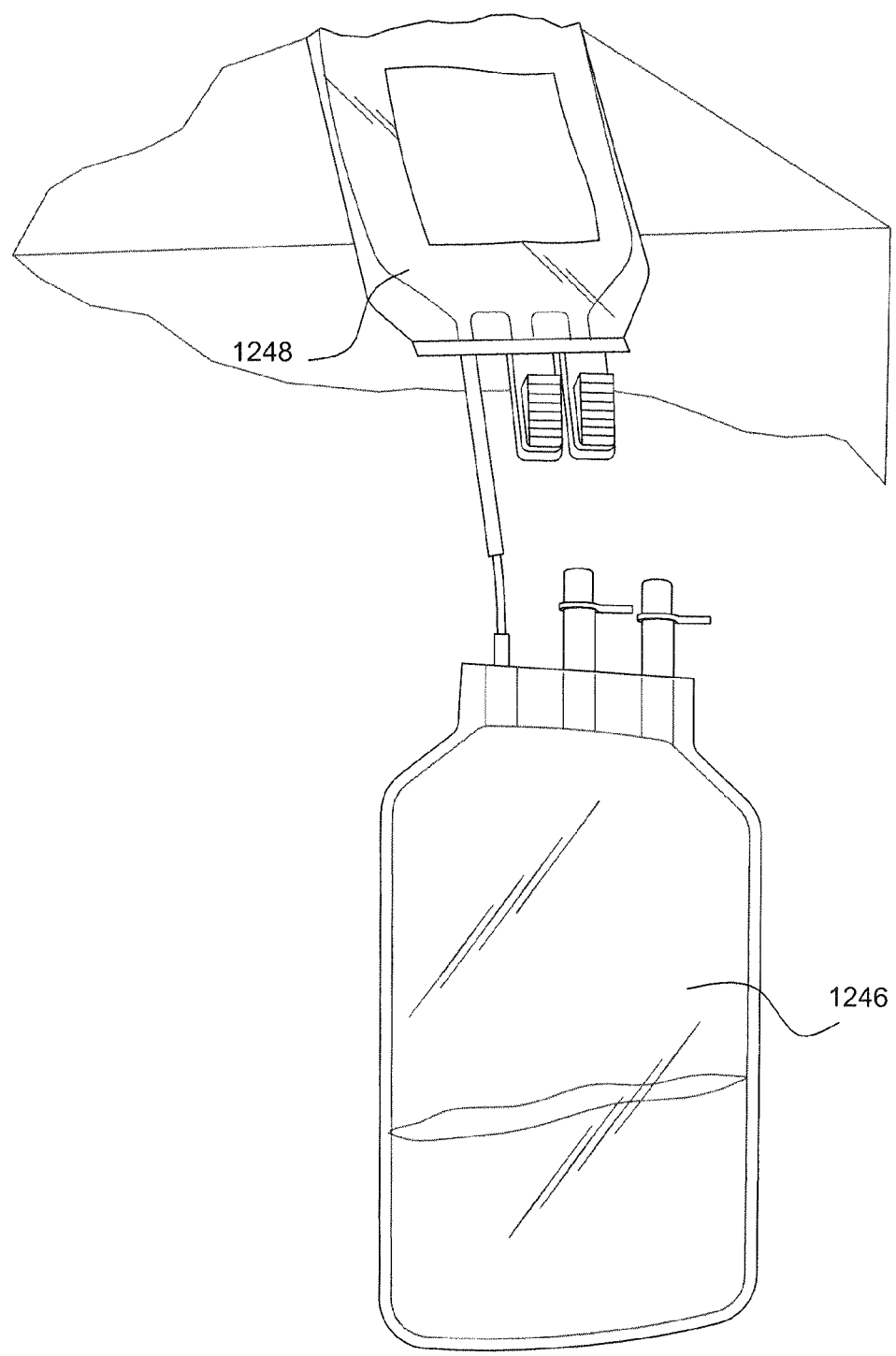
FIG. 12. Direct rehydration of freeze-dried plasma in the lyo-bag using a sterilely attached rehydration bag. Reconstitution may be accomplished also using a syringe instead of a rehydration bag.

6. A ready to use package containing the lyo-bag with the dry product attached to a rehydration bag was assembled and sealed in a moisture-resistant over-pouch (FIGS. 11-13).

A container for plasma lyoptilization the lyo-bag developed by Circular Technology, Inc. was tested (FIGS. 1-2).

Figure 3:
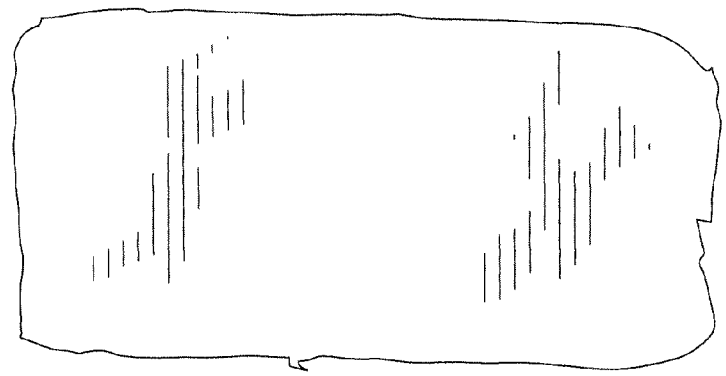
FIG. 3 (prior art). Freeze-Drying of plasma in a flexible lyo-bag without a supportive system showing contamination of the internal side of the breathable membrane with the partially dried plasma.
Figure 4:
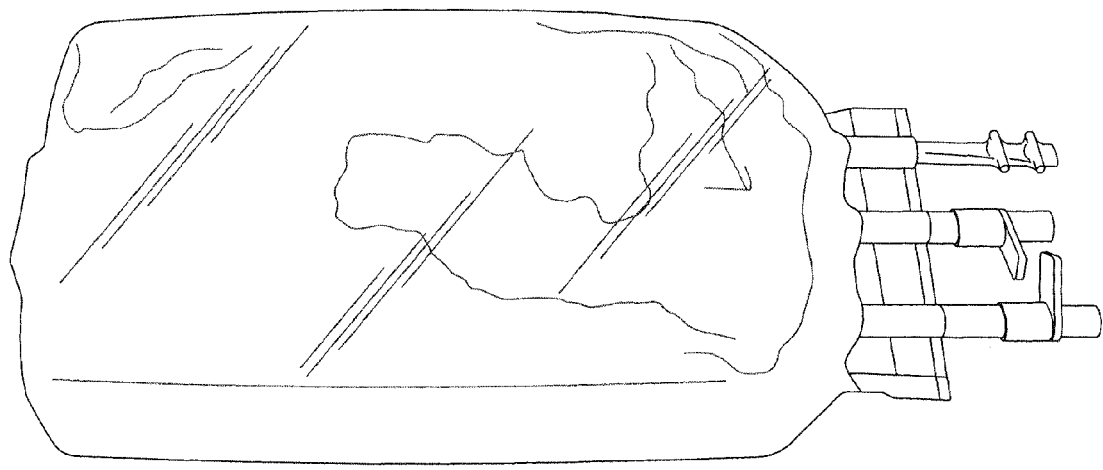
FIG. 4 (prior art). Freeze-Drying of plasma in a flexible lyo-bag without a supportive system showing the folded flexible bottom wall and large pockets of wet plasma in the folds.

Freeze-Drying of Plasma in a Flexible Lyo-Bag without a Supportive System:

FIG. 3 shows contamination of the internal side of the breathable membrane with the partially dried plasma. FIG. 4 shows the folded flexible bottom wall and large pockets of wet plasma in the folds.

Implementing the Frame Supportive System

FIG. 5 shows the top flexible membranous wall secured on top of the solid walls of a removable frame. This keeps the membrane from contacting the product before and during lyophilization.

FIG. 6 shows a flexible magnetic sheet attached to the bottom wall. The container is placed then on a steel tray to conduct lyophilization. The magnetic force keeps the pliable bottom wall from folding under vacuum.

Implementing the Gore-Tex™ Supportive System

FIG. 7 shows the bottom view of a container for plasma lyophilization with the original top membrane removed and a new Gore-Tex™ membrane sealed to the outwardly directed plastic strip (732). This keeps the membrane from contacting the product before and during lyophilization.

FIG. 8 shows the top view of the plasma lyophilization container with the new Gore-Tex™ membrane (734) affixed with tape (736) to the outward directed plastic strip.

FIG. 6 shows a flexible magnetic sheet 628 attached to the bottom wall. The container is placed then on a steel tray to conduct lyophilization. The magnetic force keeps the pliable bottom wall from folding under vacuum.

Freeze-Drying of Plasma in a Flexible Lyo-Bag Using the Supportive System

Figure 9:
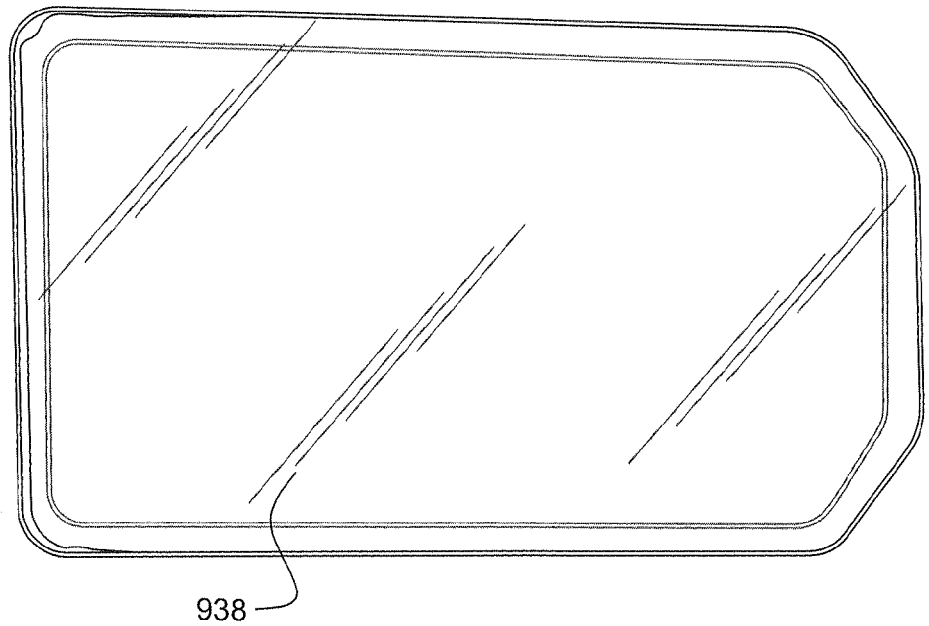
FIG. 9. Freeze-Drying of plasma in a flexible lyo-bag using the supportive system showing a clean internal surface of the breathable membrane indicating that there was no contact between the product and the membrane during lyophilization.

FIG. 9 shows a clean internal surface of the breathable membrane (938) indicating that there was no contact between the product and the membrane during lyophilization.

Figure 10:
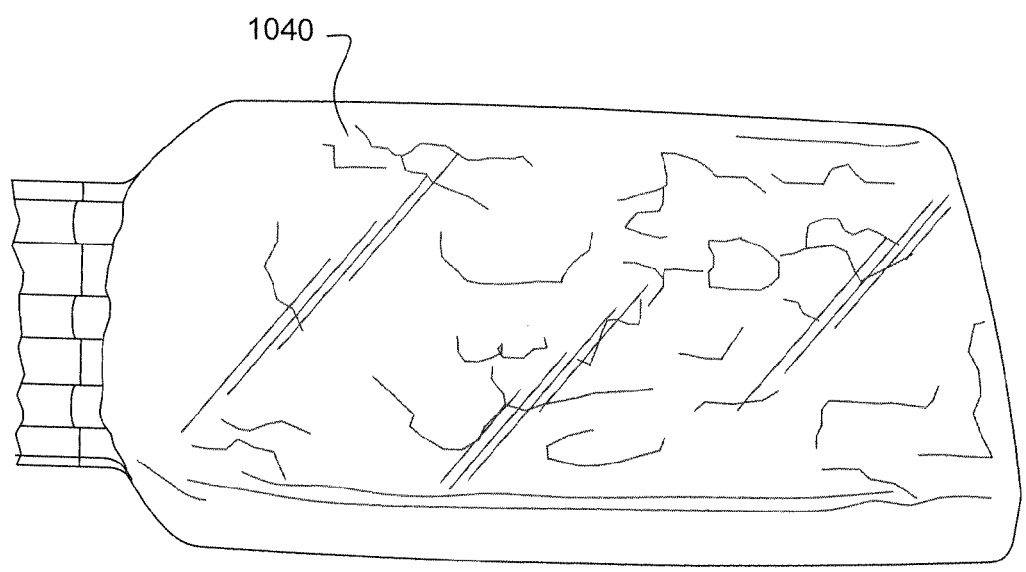
FIG. 10. Freeze-Drying of plasma in a flexible lyo-bag using the supportive system showing the bottom wall of the lyo-bag and the completely dried plasma product inside the lyo-bag, indicating that the bottom did not fold during the process of lyophilization maintaining an intimate thermal contact with the shelf.

FIG. 10 shows the bottom wall (1040) of the lyo-bag and the completely dried plasma product inside the lyo-bag, indicating that the bottom did not fold during the process of lyophilization maintaining an intimate thermal contact with the shelf and that there was no contact between the product and the membrane during lyophilization.

FIG. 11 shows the lyo-bag (1142) with the freeze-dried plasma is sterilely attached to a rehydration bag (1144) with the necessary amount of reagent grade water.

FIG. 12 show direct rehydration of freeze-dried plasma in the lyo-bag (1246) using a sterilely attached rehydration bag (1248). Reconstitution rnay be accomplished also using a syringe instead of a rehydration bag.

FIG. 13 shows a moisture-resistant overpouch (1350) is used to package the lyo-bag (1352) with the dry plasma and the rehydration bag. Two packaging modes can be utilized: 1) package the rehydration bag empty to ease the shipment and have it filled with water as it arrives in the field or 2) package the bag already filled with the necessary amount of reagent grade water.

Other embodiments and uses of the invention will be apparent to those skilled in the art from consideration of the specification and practice of the invention disclosed herein. All references cited herein, including all publications, U.S. and foreign patents and patent applications, are specifically and entirely incorporated by reference. It is intended that the specification and examples be considered exemplary only.

TABLE 1

| OctaPlas | PT(sec) | APTT (sec) | TT(sec) | Fib(mg/dl) | V(%) | VIII(%) |
| --- | --- | --- | --- | --- | --- | --- |
| PreLyo | 14 ± 0.219 | 32.5 ± 0.712 | 18.5 ± 0.519 | 315 ± 0.165 | 62 ± 5.831 | 59 ± 9.772 |
| Post Lyo | 14.1 ± 0.306 | 35.8 ± 0.765 | 18.2 ± 0.644 | 315 ± 0.629 | 54 ± 5.360 | 48 ± 9.894 |

The invention claimed is:

1. A method of providing adequate support to a flexible lyophilization container during the process of lyophilizing a biological solution in the flexible lyophilization container, the method comprising:
   providing a flexible lyophilization container having a top flexible membrane and an inwardly directed plastic strip to which the top flexible membrane is attached, said inwardly directed plastic strip attached to a top edge of the flexible lyophilization container and directed inwardly towards the container;
   removing the top flexible membrane along with the inwardly directed plastic strip; attaching a plastic strip directed outwardly away from the container to the top edge of the flexible lyophilization container to serve as a platform for a replacement top flexible membrane;
   affixing a replacement top flexible membrane to the top edge of the flexible lyophilization container;
   affixing a bottom wall of the lyophilization container to a support sheet; and
   placing the support sheet on a tray.

2. The method of claim 1, wherein the replacement top flexible membrane is expanded polytetrafluoroethylene or non-woven spunbonded olefin membrane.

3. The method of claim 1, wherein the support sheet is magnetic.

4. The method of claim 1, wherein the affixing of a replacement top flexible membrane is achieved with double-sided tape.

5. The method of claim 4, wherein the double-sided tape is thermally conductive.

6. The method of claim 1, wherein the affixing of the bottom wall is achieved with double sided tape.

* * * * *